(12) United States Patent
Klemarczyk et al.

(10) Patent No.: US 9,969,863 B2
(45) Date of Patent: May 15, 2018

(54) CURE ACCELERATORS FOR ANAEROBIC CURABLE COMPOSITIONS

(71) Applicant: Henkel IP & Holding GmbH, Duesseldorf (DE)

(72) Inventors: Philip T. Klemarczyk, Canton, CT (US); Jianping Liu, South Glastonbury, CT (US); Ory Hajatpour, Naas (IE); David P. Birkett, Naas (IE)

(73) Assignee: Henkel IP & Holding GmbH, Duesseldorf (DE)

( * ) Notice: Subject to any disclaimer, the term of this patent is extended or adjusted under 35 U.S.C. 154(b) by 0 days. days.

(21) Appl. No.: 15/417,884

(22) Filed: Jan. 27, 2017

(65) Prior Publication Data

US 2017/0137606 A1 May 18, 2017

Related U.S. Application Data (63) Continuation of application No. PCT/US2015/038421, filed on Jun. 30, 2015.

(60) Provisional application No. 62/030,932, filed on Jul. 30, 2014.

(51) Int. Cl.

| C08K 5/3417 | (2006.01) |
|---|---|
| C08K 5/3437 | (2006.01) |
| C08L 35/02 | (2006.01) |
| C09J 135/02 | (2006.01) |
| C07D 209/08 | (2006.01) |
| C09J 4/00 | (2006.01) |
| C09J 4/06 | (2006.01) |
| C08F 122/14 | (2006.01) |
| C07D 215/08 | (2006.01) |

(52) U.S. Cl.
CPC .......... *C08K 5/3417* (2013.01); *C07D 209/08* (2013.01); *C07D 215/08* (2013.01); *C08F 122/14* (2013.01); *C08K 5/3437* (2013.01); *C08L 35/02* (2013.01); *C09J 4/00* (2013.01); *C09J 4/06* (2013.01); *C09J 135/02* (2013.01)

(58) Field of Classification Search
CPC .. C07D 209/04; C07D 209/08; C07D 215/08; C08F 122/14; C08K 5/20; C08K 5/3417; C08K 5/3437; C08L 33/04; C08L 35/02; C09J 133/04; C09J 135/02; C09J 4/00; C09J 4/06; C09J 133/06
USPC .................................................. 526/204
See application file for complete search history.

(56) References Cited

U.S. PATENT DOCUMENTS

| 3,218,305 A | 11/1965 | Krieble |
|---|---|---|
| 3,794,610 A | 2/1974 | Bachmann |
| 3,970,505 A | 7/1976 | Hauser et al. |
| 4,174,311 A | 11/1979 | Nakano et al. |
| 4,180,640 A | 12/1979 | Doherty et al. |
| 4,287,330 A | 9/1981 | Rich |
| 4,287,350 A | 9/1981 | Huellstrung et al. |
| 4,321,349 A | 2/1982 | Rich |
| 4,324,349 A | 4/1982 | Kaufman |
| 4,647,584 A | 3/1987 | Takahashi et al. |
| 5,411,988 A | 5/1995 | Bockow et al. |
| 5,605,999 A | 2/1997 | Chu et al. |
| 5,811,473 A | 9/1998 | Rich et al. |
| 6,391,993 B1 | 5/2002 | Attarwala et al. |
| 6,583,289 B1 | 6/2003 | McArdle et al. |
| 6,835,762 B1 | 12/2004 | Klemarczyk et al. |
| 6,897,277 B1 | 5/2005 | Klemarczyk |
| 6,958,368 B1 | 10/2005 | Klemarczyk et al. |
| 8,362,112 B2 | 1/2013 | Birkett et al. |
| 8,481,659 B2 | 7/2013 | Birkett et al. |
| 2004/0236109 A1 | 11/2004 | Van Straten et al. |

(Continued)

FOREIGN PATENT DOCUMENTS

| CN | 101328395 | 12/2008 |
|---|---|---|
| DE | 1817989 | 12/1976 |
| DE | 2806701 | 8/1978 |

(Continued)

OTHER PUBLICATIONS

International Search Report issued in connection with International Patent Application No. PCT/US2015/038421 dated Sep. 17, 2015.

(Continued)

*Primary Examiner* — Ling Choi
*Assistant Examiner* — Chun-Cheng Wang
(74) *Attorney, Agent, or Firm* — Steven C. Bauman (57) ABSTRACT

Cure accelerators for anaerobic curable compositions, such as adhesives and sealants, are provided, and which are defined with reference to the aromatic amides shown in structure I

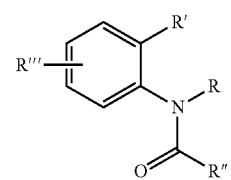

where R and R" are each independently $C_{1-10}$ alkyl, and R' is H or $C_{1-10}$ alkyl or R and R' together may form a four to seven membered ring fused to the benzene ring, and where R''' is optional, but when R''' is present, R''' is halogen, alkyl, alkenyl, cycloalkyl, hydroxyalkyl, hydroxyalkenyl, alkoxy, amino, alkylene- or alkenylene-ether, alkylene (meth)acrylate, carbonyl, carboxyl, nitroso, sulfonate, hydroxyl or haloalkyl.

9 Claims, 5 Drawing Sheets

(56) References Cited

U.S. PATENT DOCUMENTS

2012/0157641 A1* 6/2012 Birkett ................ C07D 209/08
526/204

FOREIGN PATENT DOCUMENTS

| | | |
|---|---|---|
| FR | 1581361 | 9/1969 |
| JP | 52015530 | 2/1977 |
| JP | 54021441 | 2/1979 |
| JP | 07308757 | 11/1995 |
| RU | 2347570 | 2/2009 |
| SU | 367599 | 3/1973 |
| WO | 2010/127053 | 11/2010 |
| WO | 2010/127055 | 11/2010 |

OTHER PUBLICATIONS

R.D. Rich, "Anaerobic Adhesives" in Handbook of Adhesive Technology, 29, 467-79, A. Pizzi and K.L. Mittal, eds., Marcel Dekker, Inc., New York (1994), and references cited therein.

Cordeiro, Alessandra et al. Synthesis of 6-Nitro-1,2,3,4-tetrahydroquinoline; An Experimental and Theoretical Study of Regioselective Nitration. European Journal of Organic Chemistry, 2011, pp. 1504-1513.

\* cited by examiner

CURE ACCELERATORS FOR ANAEROBIC CURABLE COMPOSITIONS

BACKGROUND

Field

Cure accelerators for anaerobic curable compositions, such as adhesives and sealants, are provided, and which are defined with reference to the aromatic amides shown in structure I

I where R and R" are each independently $C_{1-10}$ alkyl, and R' is H or $C_{1-10}$ alkyl or R and R' together may form a four to seven membered ring fused to the benzene ring, and where R'" is optional, but when R'" is present, R'" is halogen, alkyl, alkenyl, cycloalkyl, hydroxyalkyl, hydroxyalkenyl, alkoxy, amino, alkylene- or alkenylene-ether, alkylene (meth)acrylate, carbonyl, carboxyl, nitroso, sulfonate, hydroxyl or haloalkyl.

Brief Description of Related Technology

Anaerobic adhesive compositions generally are well-known. See e.g. R. D. Rich, "Anaerobic Adhesives" in *Handbook of Adhesive Technology*, 29, 467-79, A. Pizzi and K. L. Mittal, eds., Marcel Dekker, Inc., New York (1994), and references cited therein. Their uses are legion and new applications continue to be developed.

Conventional anaerobic adhesives ordinarily include a free-radically polymerizable acrylate ester monomer, together with a peroxy initiator and an inhibitor component. Often, such anaerobic adhesive compositions also contain accelerator components to increase the speed with which the composition cures.

Desirable anaerobic cure-inducing compositions to induce and accelerate cure may include one or more of saccharin, toluidines, such as N,N-diethyl-p-toluidine ("DE-p-T") and N,N-dimethyl-o-toluidine ("DM-o-T"), and acetyl phenylhydrazine ("APH") with maleic acid. See e.g. U.S. Pat. No. 3,218,305 (Krieble), U.S. Pat. No. 4,180,640 (Melody), U.S. Pat. No. 4,287,330 (Rich) and U.S. Pat. No. 4,321,349 (Rich).

Saccharin and APH are used as standard cure accelerator components in anaerobic adhesive cure systems. Indeed, many of the LOCTITE-brand anaerobic adhesive products currently available from Henkel Corporation use either saccharin alone or both saccharin and APH. These chemicals have scrutinized in certain parts of the world, and thus efforts have been undertaken to identify candidates as replacements.

Examples of other curatives for anaerobic adhesives include thiocaprolactam (e.g., U.S. Pat. No. 5,411,988) and thioureas [e.g., U.S. Pat. No. 3,970,505 (Hauser) (tetramethyl thiourea), German Patent Document Nos. DE 1 817 989 (alkyl thioureas and N,N'-dicyclohexyl thiourea) and 2 806 701 (ethylene thiourea), and Japanese Patent Document No. JP 07-308,757 (acyl, alkyl, alkylidene, alkylene and alkyl thioureas)], certain of the latter of which had been used commercially up until about twenty years ago.

Trithiadiaza pentalenes have also been shown to be effective as curatives for anaerobic adhesive compositions. The addition of these materials into anaerobic adhesives as a replacement for conventional curatives (such as APH) surprisingly provides at least comparable cure speeds and physical properties for the reaction products formed therefrom. See U.S. Pat. No. 6,583,289 (McArdle).

U.S. Pat. No. 6,835,762 (Klemarczyk) provides an anaerobic curable composition based on a (meth)acrylate component with an anaerobic cure-inducing composition substantially free of acetyl phenylhydrazine and maleic acid and an anaerobic cure accelerator compound having the linkage —C(=O)—NH—NH— and an organic acid group on the same molecule, provided the anaerobic cure accelerator compound excludes 1-(2-carboxyacryloyl)-2-phenylhydrazine. The anaerobic cure accelerator is embraced by:

where $R^1$-$R^7$ are each independently selected from hydrogen and $C_{1-4}$; Z is a carbon-carbon single bond or carbon-carbon double bond; q is 0 or 1; and p is between 1 and 5, examples of which are 3-carboxyacryloyl phenylhydrazine, methyl-3-carboxyacryloyl phenylhydrazine, 3-carboxypropanoyl phenylhydrazine, and methylene-3-carboxypropanoyl phenylhydrazine.

U.S. Pat. No. 6,897,277 (Klemarczyk) provides an anaerobic curable composition based on a (meth)acrylate component with an anaerobic cure-inducing composition substantially free of saccharin and an anaerobic cure accelerator compound within the following structure where R is selected from hydrogen, halogen, alkyl, alkenyl, hydroxyalkyl, hydroxyalkenyl, carboxyl, and sulfonato, and $R^1$ is selected from hydrogen, alkyl, alkenyl, hydroxyalkyl, hydroxyalkenyl, and alkaryl, an example of which is phenyl glycine and N-methyl phenyl glycine.

U.S. Pat. No. 6,958,368 (Messana) provides an anaerobic curable composition. This composition is based on a (meth) acrylate component with an anaerobic cure-inducing composition substantially free of saccharin and within the following structure where Y is an aromatic ring, optionally substituted at up to five positions by $C_{1-6}$ alkyl or alkoxy, or halo groups; A is C=O, S=O or O=S=O; X is NH, O or S and Z is an aromatic ring, optionally substituted at up to five positions by $C_{1-6}$ alkyl or alkoxy, or halo groups, or Y and Z taken together may join to the same aromatic ring or aromatic ring system, provided that when X is NH, o-benzoic sulfimide is excluded from the structure. Examples of the anaerobic cure accelerator compound embraced by the structure above include 2-sulfobenzoic acid cyclic anhydride, and 3H-1,2-benzodithiol-3-one-1,1-dioxide.

Three Bond Co. Ltd., Tokyo, Japan has in the past described as a component in anaerobic adhesive and sealant compositions a component called tetrahydroquinoline ("THQ").

And more recently Henkel Corporation has demonstrated the efficacy of new cure accelerators. The first class is within the structure below where X is H, $C_{1-20}$ alkyl, $C_{2-20}$ alkenyl, or $C_{7-20}$ alkaryl, any of the latter three of which may be interrupted by one or more hereto atoms or functionalized by one or more groups selected from —OH, —NH$_2$ or —SH, or X and Y taken together form a carbocyclic ring having from 5-7 ring atoms; Z is O, S, or NX', where X' is H, $C_{1-20}$ alkyl, $C_{2-20}$ alkenyl, or $C_{7-20}$ alkaryl, any of the latter three of which may be interrupted by one or more hereto atoms or functionalized by one or more groups selected from —OH, —NH$_2$ or —SH; R is optional but when present may occur up to 3 times on the aromatic ring and when present is $C_{1-20}$ alkyl, $C_{2-20}$ alkenyl, or $C_{7-20}$ alkaryl, any of the latter three of which may be interrupted by one or more hereto atoms or functionalized by one or more groups selected from —OH, —NH$_2$ or —SH; and n is 0 and 1 and z is 1-3, provided that when X is H, z is not 2 and is preferably 1. More specifically, THQ-based or indoline-based adducts may be embraced thereby. (See U.S. Pat. No. 8,481,659.)

The second class is within the structure below where X is $C_{1-20}$ alkyl, $C_{2-20}$ alkenyl, or $C_{7-20}$ alkaryl, any of which may be interrupted by one or more hereto atoms, and which are functionalized by at least one and preferably at least two groups selected from —OH, —NH$_2$ or —SH and z is 1-3. (See U.S. Pat. No. 8,362,112.)

Notwithstanding the state of the art, there is an on-going desire to find alternative technologies for anaerobic cure accelerators to differentiate existing products and provide supply assurances in the event of shortages or cessation of supply of raw materials. Moreover, since certain of the raw materials used in conventional anaerobic cure inducing compositions have to one degree or another come under regulatory scrutiny, alternative components for anaerobic cure inducing compositions would be desirable. Accordingly, it would be desirable to identify new materials that function as cure components in the cure of anaerobically curable compositions.

SUMMARY

Cure accelerators for anaerobic curable compositions, such as adhesives and sealants, are provided as another option to satisfy that desire.

Cure accelerators for anaerobic curable compositions, such as adhesives and sealants, are provided, and which are defined with reference to the aromatic amides shown in structure I where R and R" are each independently $C_{1-10}$ alkyl, and R' is H or $C_{1-10}$ alkyl or R and R' together may form a four to seven membered ring fused to the benzene ring, and where R''' is optional, but when R''' is present, R''' is halogen, alkyl, alkenyl, cycloalkyl, hydroxyalkyl, hydroxyalkenyl, alkoxy, amino, alkylene- or alkenylene-ether, alkylene (meth)acrylate, carbonyl, carboxyl, nitroso, sulfonate, hydroxyl or haloalkyl.

Compounds within structure I may be prepared as follows:

where R, R' and R" are each as defined above. While an acid chloride is shown as the reactant in this scheme, other acid halides may be used as well.

The cure accelerator embraced by structure I is useful in anaerobic curable compositions, such as adhesives and sealants.

Methods of preparing and using anaerobically curable adhesive and sealant compositions prepared with the cure accelerators within structure I also are provided, as well are the reaction products of the anaerobically curable adhesive and sealant compositions.

DETAILED DESCRIPTION

As noted above, cure accelerators for anaerobic curable compositions, such as adhesives and sealants, are provided, and which are defined with reference to the aromatic amides shown in structure I

I where R and R" are each independently $C_{1-10}$ alkyl, and R' is H or $C_{1-10}$ alkyl or R and R' together may form a four to seven membered ring fused to the benzene ring, and where R'" is optional, but when R'" is present, R'" is halogen, alkyl, alkenyl, cycloalkyl, hydroxyalkyl, hydroxyalkenyl, alkoxy, amino, alkylene- or alkenylene-ether, alkylene (meth)acrylate, carbonyl, carboxyl, nitroso, sulfonate, hydroxyl or haloalkyl.

As noted above, compounds within structure I may be prepared as follows:

where R and R' are each independently alkyl (such as methyl, ethyl, propyls or butyls), R' is H or alkyl (such as methyl, ethyl, propyls or butyls), or R and R' together may form a four to seven membered ring fused to the benzene ring, and where R'" is optional, but when R'" is present, R'" is halogen, alkyl, alkenyl, cycloalkyl, hydroxyalkyl, hydroxyalkenyl, alkoxy, amino, alkylene- or alkenylene-ether, alkylene (meth)acrylate, carbonyl, carboxyl, nitroso, sulfonate, hydroxyl or haloalkyl. While an acid chloride is shown as the reactant in this scheme, other acid halides may be used as well.

Desirably, the aromatic amide shown in structure I is based on either tetrahydroquinoline ("THQ"), indoline or N-methyl aniline. Thus, the compound of structure I when based on THQ, indoline or N-methyl aniline, respectively, is an N-acetyl derivative thereof, namely, N-acetyl tetrahydroquinoline, N-acetyl indoline or N-acetyl, N-methyl aniline, respectively.

The addition of such compounds as cure accelerators into anaerobic adhesives as a replacement for some or all of the amount of conventional anaerobic cure accelerators (such as the toluidines, DE-p-T and DM-o-T, and/or APH) surprisingly develops ultimate adhesive properties, while are comparable to those observed from conventional anaerobic curable compositions.

Methods of preparing the aromatic amides of structure I are provided. The methods involve reacting: (a) at least one compound selected from compounds within the following structure A:

where R, R' and R'" are as described above and (b) an acid halide, such as acetyl chloride. The reaction should desirably proceed in the presence of a base, such as a pyridine.

Examples of these compounds include:

Tetrahydroquinoline (THQ)    Indoline    N-Methyl aniline

In preparing the aromatic amides of structure I, the reaction may be conducted in the presence of a solvent, in which case the compound of structure A may be dissolved in solvent prior to reaction with the acid halide, or vice versa. And the reaction desirably is conducted in the presence of a base. Here, pyridine is shown; but other bases may be used as well.

The temperature employed in the reaction may also vary over a wide range. Where the components are combined in approximately chemical equivalent amounts or with one in slight excess over the other, useful temperatures may vary from room temperature or below, e.g., 10° C. to 15° C., up to and including temperatures of 100° C.

The so formed compounds may be purified to remove impurities, such as reaction by-products or impurities that accompany the reactants. The compounds can be purified for example by distillation, filtration, stripping, chromatography, or recrystallization, such that the purified reaction product(s) are essentially free of impurities, or comprise less than about 1 weight percent of impurities.

Anaerobic curable compositions generally are based on a (meth)acrylate component, together with an anaerobic cure-inducing composition. In the present invention, the anaerobic cure-inducing composition, has at least reduced levels of APH or toluidines (such as about 50% or less by weight of that which is used in conventional anaerobic curable compositions, for instance less than about 10 weight percent, such as less than about 5 weight percent, and desirably less than about 1 weight percent) or is free of APH or toluidines altogether. In place of some or all of APH or toluidines is the inventive cure accelerator—this is, compounds embraced by structure I.

(Meth)acrylate monomers suitable for use as the (meth)acrylate component in the present invention may be selected from a wide variety of materials, such as those represented by $H_2C=CGCO_2R^8$, where G may be hydrogen, halogen or alkyl groups having from 1 to about 4 carbon atoms, and $R^8$ may be selected from alkyl, cycloalkyl, alkenyl, cycloalkenyl, alkaryl, alkaryl or aryl groups having from 1 to about 16 carbon atoms, any of which may be optionally substituted or interrupted as the case may be with silane, silicon, oxygen, halogen, carbonyl, hydroxyl, ester, carboxylic acid, urea, urethane, carbonate, amine, amide, sulfur, sulfonate, sulfone and the like.

Additional (meth)acrylate monomers suitable for use herein include polyfunctional (meth)acrylate monomers, for example di- or tri-functional (meth)acrylates such as polyethylene glycol di(meth)acrylates, tetrahydrofuran (meth)acrylates and di(meth)acrylates, hydroxypropyl (meth)acrylate ("HPMA"), hexanediol di(meth)acrylate, trimethylol propane tri(meth)acrylates ("TMPTMA"), diethylene glycol dimethacrylate, triethylene glycol dimethacrylates ("TRIEGMA"), tetraethylene glycol di(meth)acrylates, dipropylene glycol di(meth)acrylates, di-(pentamethylene glycol) di(meth)acrylates, tetraethylene diglycol di(meth)acrylates, diglycerol tetra(meth)acrylates, tetramethylene di(meth)acrylates, ethylene di(meth)acrylates, neopentyl glycol di(meth)acrylates, and bisphenol-A mono and di(meth)acrylates, such as ethoxylated bisphenol-A (meth)acrylate ("EBIPMA"), and bisphenol-F mono and di(meth)acrylates, such as ethoxylated bisphenol-A (meth)acrylate.

Still other (meth)acrylate monomers that may be used herein include silicone (meth)acrylate moieties ("SiMA"), such as those taught by and claimed in U.S. Pat. No. 5,605,999 (Chu), incorporated herein by reference.

Other suitable monomers include polyacrylate esters represented by the formula where $R^4$ is a radical selected from hydrogen, halogen or alkyl of from 1 to about 4 carbon atoms; q is an integer equal to at least 1, and preferably equal to from 1 to about 4; and X is an organic radical containing at least two carbon atoms and having a total bonding capacity of q plus 1. With regard to the upper limit for the number of carbon atoms in X, workable monomers exist at essentially any value. As a practical matter, however, a general upper limit is about 50 carbon atoms, such as desirably 30, and desirably about 20.

For example, X can be an organic radical of the formula:

where each of $Y^1$ and $Y^2$ is an organic radical, such as a hydrocarbon group, containing at least 2 carbon atoms, and desirably from 2 to about 10 carbon atoms, and Z is an organic radical, preferably a hydrocarbon group, containing at least 1 carbon atom, and preferably from 2 to about 10 carbon atoms.

Other classes of useful monomers are the reaction products of di- or tri-alkylolamines (e.g., ethanolamines or propanolamines) with acrylic acids, such as are disclosed in French Pat. No. 1,581,361.

Examples of useful acrylic ester oligomers include those having the following general formula:

where $R^5$ represents a radical selected from hydrogen, lower alkyl of from 1 to about 4 carbon atoms, hydroxy alkyl of from 1 to about 4 carbon atoms, or where $R^4$ is a radical selected from hydrogen, halogen, or lower alkyl of from 1 to about 4 carbon atoms; $R^6$ is a radical selected from hydrogen, hydroxyl, or m is an integer equal to at least 1, e.g., from 1 to about 15 or higher, and desirably from 1 to about 8; n is an integer equal to at least 1, e.g., 1 to about 40 or more, and desirably between about 2 and about 10; and p is 0 or 1.

Typical examples of acrylic ester oligomers corresponding to the above general formula include di-, tri- and tetraethyleneglycol dimethacrylate; di(pentamethyleneglycol)dimethacrylate; tetraethyleneglycol diacrylate; tetraethyleneglycol di(chloroacrylate); diglycerol diacrylate; diglycerol tetramethacrylate; butyleneglycol dimethacrylate; neopentylglycol diacrylate; and trimethylolpropane triacrylate.

While di- and other polyacrylate esters, and particularly the polyacrylate esters described in the preceding paragraphs, can be desirable, monofunctional acrylate esters (esters containing one acrylate group) also may be used. When dealing with monofunctional acrylate esters, it is highly preferable to use an ester which has a relatively polar alcoholic moiety. Such materials are less volatile than low molecular weight alkyl esters and, more important, the polar group tends to provide intermolecular attraction during and after cure, thus producing more desirable cure properties, as well as a more durable sealant or adhesive. Most preferably, the polar group is selected from labile hydrogen, heterocyclic ring, hydroxy, amino, cyano, and halo polar groups. Typical examples of compounds within this category are cyclohexylmethacrylate, tetrahydrofurfuryl methacrylate, hydroxyethyl acrylate, hydroxypropyl methacrylate, t-butylaminoethyl methacrylate, cyanoethylacrylate, and chloroethyl methacrylate.

Another useful class of monomers is prepared by the reaction of a monofunctionally substituted alkyl or aryl acrylate ester containing an active hydrogen atom on the functional substituent. This monofunctional, acrylate-terminated material is reacted with an organic polyisocyanate in suitable proportions so as to convert all of the isocyanate groups to urethane or ureido groups. The monofunctional alkyl and aryl acrylate esters are preferably the acrylates and methacrylates containing hydroxy or amino functional groups on the nonacrylate portion thereof. Acrylate esters suitable for use have the formula where X is selected from —O— and where $R^9$ is selected from hydrogen or lower alkyl of 1 through 7 carbon atoms; $R^7$ is selected from hydrogen, halogen (such as chlorine) or alkyl (such as methyl and ethyl radicals); and $R^8$ is a divalent organic radical selected from lower alkylene of 1 through 8 carbon atoms, phenylene and naphthylene. These groups upon proper reaction with a polyisocyanate, yield a monomer of the following general formula:

where n is an integer from 2 to about 6; B is a polyvalent organic radical selected from alkyl, alkenyl, cycloalkyl, cycloalkenyl, aryl, alkaryl, alkaryl and heterocyclic radicals both substituted and unsubstituted; and $R^7$, $R^8$ and X have the meanings given above.

Of course, combinations of these (meth)acrylate monomers may also be used.

The (meth)acrylate component may comprise from about 10 to about 90 percent by weight of the composition, such as about 60 to about 90 percent by weight, based on the total weight of the composition.

Additional components have in the past been included in traditional anaerobic adhesive and/or sealant compositions to alter the physical properties of either the formulation or the reaction products thereof. For instance, one or more of thermal resistance-conferring co-reactants (such as maleimide components), diluent components reactive at elevated temperature conditions, mono- or poly-hydroxyalkanes, polymeric plasticizers, thickeners, non-reactive plasticizers, fillers, toughening agents (such as elastomers and rubbers) and chelators (see U.S. Pat. No. 6,391,993, incorporated herein by reference) may be included to modify the physical property and/or cure profile of the formulation and/or the strength or temperature resistance of the cured adhesive.

When used, the co-reactant, reactive diluent, plasticizer, mono- or poly-hydroxyalkanes, filler and/or toughening agent may be present in an amount within the range of about 1 percent to about 30 percent by weight, based on the total weight of the composition.

The inventive compositions may also include other conventional components, such as free radical initiators, free radical co-accelerators, and inhibitors of free radical generation, as well as metal catalysts.

A number of well-known initiators of free radical polymerization are typically incorporated into anaerobic curable compositions including, without limitation, hydroperoxides, such as cumene hydroperoxide ("CHP"), para-menthane hydroperoxide, t-butyl hydroperoxide ("TBH") and t-butyl perbenzoate. Other peroxides include benzoyl peroxide, dibenzoyl peroxide, 1,3-bis(t-butylperoxyisopropyl)benzene, diacetyl peroxide, butyl 4,4-bis(t-butylperoxy)valerate, p-chlorobenzoyl peroxide, t-butyl cumyl peroxide, t-butyl perbenzoate, di-t-butyl peroxide, dicumyl peroxide, 2,5-dimethyl-2,5-di-t-butylperoxyhexane, 2,5-dimethyl-2,5-di-t-butyl-peroxyhex-3-yne, 4-methyl-2,2-di-t-butylperoxypentane, t-amyl hydroperoxide, 1,2,3,4-tetramethylbutyl hydroperoxide and combinations thereof.

Such peroxides are typically employed in the present invention in the range of from about 0.1 to about 10 percent by weight, based on the total weight of the composition, with about 1 to about 5 percent by weight being desirable.

As noted, conventional accelerators of free radical polymerization may also be used in conjunction with the inventive anaerobic cure accelerators, though in amounts less than that used in the past. Such accelerators are typically of the hydrazine variety (e.g., APH), as disclosed in U.S. Pat. No. 4,287,350 (Rich) and U.S. Pat. No. 4,321,349 (Rich). Maleic acid is ordinarily added to APH-containing anaerobic cure inducing compositions.

Co-accelerators of free radical polymerization may also be used in the compositions of the present invention including, without limitation, organic amides and imides, such as benzoic sulfimide (also known as saccharin) (see U.S. Pat. No. 4,324,349).

Stabilizers and inhibitors (such as phenols including hydroquinone and quinones) may also be employed to control and prevent premature peroxide decomposition and polymerization of the composition of the present invention, as well as chelating agents [such as the tetrasodium salt of ethylenediamine tetraacetic acid ("EDTA")] to trap trace amounts of metal contaminants therefrom. When used, chelating agents may ordinarily be present in the compositions in an amount from about 0.001 percent by weight to about 0.1 percent by weight, based on the total weight of the composition.

The inventive cure accelerators may be used in amounts of about 0.1 to about 5 percent by weight, such as about 1 to about 2 percent by weight, based on the total weight of the composition. When used in combination with conventional accelerators (though at lower levels than such conventional accelerators), the inventive accelerators should be used in amounts of about 0.01 to about 5 percent by weight, such as about 0.02 to about 2 percent by weight, based on the total weight of the composition.

The present invention also provides methods of preparing and using the inventive anaerobically curable compositions, as well as reaction products of the compositions.

The compositions of the present invention may be prepared using conventional methods which are well known to those persons of skill in the art. For instance, the components of the inventive anaerobic adhesive and sealant compositions may be mixed together in any convenient order consistent with the roles and functions the components are to perform in the compositions. Conventional mixing techniques using known apparatus may be employed.

The compositions of this invention may be applied to a variety of substrates to perform with the desired benefits and advantages described herein. For instance, appropriate substrates may be constructed from steel, brass, copper, aluminum, zinc, and other metals and alloys, ceramics and thermosets. An appropriate primer for anaerobic curable compositions may be applied to a surface of the chosen substrate to enhance cure rate. Or, the inventive anaerobic cure accelerators may be applied to the surface of a substrate as a primer. See e.g. U.S. Pat. No. 5,811,473 (Ramos).

In addition, the invention provides a method of preparing an anaerobic curable composition, a step of which includes mixing together a (meth)acrylate component, and the anaerobic cure-inducing composition comprising the combination of peroxide and aromatic amides shown in structure I.

The invention also provides a process for preparing a reaction product from the anaerobic curable composition of the present invention, the steps of which include applying the composition to a desired substrate surface and exposing the composition to an anaerobic environment for a time sufficient to cure the composition.

This invention also provides a method of using as a cure accelerator for anaerobic curable composition, aromatic amides of structure I. That method involves providing an anaerobic curable composition comprising a (meth)acrylate component; providing an anaerobic cure-inducing composition comprising the combination of peroxide and aromatic amides of structure I; and exposing the anaerobic curable composition and the cure accelerator to conditions favorable to cure the composition.

And the present invention provides a method of using an anaerobic cure accelerator compound, including (I) mixing the anaerobic cure accelerator compound in an anaerobic curable composition or (II) applying onto a surface of a substrate the anaerobic cure accelerator compound and applying thereover an anaerobic curable composition. Of course, the present invention also provides a bond formed between mated substrates with the inventive composition.

In view of the above description of the present invention, it is clear that a wide range of practical opportunities are provided. The following examples are illustrative purposes only, and are not to be construed so as to limit in any way the teaching herein.

EXAMPLES

Synthesis of Aromatic Amides of Structure I

N-Acetyl Tetrahydroquinoline

Tetrahydroquinoline (THQ)　　　　　N-Acetyl THQ

To a 1000 mL four-neck round bottom flask, equipped with a condenser, thermocouple, addition funnel, mechanical stirrer, and a nitrogen inlet, was added tetrahydroquinoline (133.0 g, 1.0 mol), pyridine (84.7 g, 1.07 mol), and i-Pr$_2$O (500 mL) with stirring. The solution was cooled to 0-5° C. in an ice bath, and acetyl chloride (83.6 g, 1.07 mol) was added dropwise with the temperature kept below 10° C. during the addition. After the addition was complete, the reaction mixture was stirred for a period of time of about 1.5 hours under ice bath cooling conditions. The ice bath was then removed, and the reaction was stirred overnight at room temperature.

The reaction mixture was added to 1000 mL of H$_2$O in a 2000 mL separatory funnel. The aqueous layer was separated, and the organic layer was washed twice with 500 mL portions of H$_2$O. The organic layer was then separated, dried over anhydrous MgSO$_4$, and filtered. Solvent was removed under reduced pressure over and the residue was distilled under vacuum (ca. 2.0 Torr). Yield=133.5 g (76%); B.P. (° C.)=117/2.0 Torr. $^1$H NMR (CDCl$_3$) δ 7.1 (m, 4, Ar—H) 3.8 (t, 2, N—CH$_2$), 2.8 (t, 2, Ar—CH$_2$), 2.1 (3, s, CH$_3$), 2.0 (m, 2, CH$_2$); $^{13}$C NMR (CDCl$_3$) δ 170, 139, 128, 126, 125, 124, 43, 27, 24, 23; IR (neat) 2942, 1647, 1578, 1489, 1371, 1328, 1257, 1204, 756 cm$^{-1}$.

N-Acetyl Indoline

Indoline　　　　　N-acetyl indoline

To a 1000 mL four-neck round bottom flask, equipped with a condenser, thermocouple, addition funnel, mechanical stirrer, and a nitrogen inlet, was added indoline (100.0 g, 0.84 mol), pyridine (69.7 g, 0.88 mol), and i-Pr$_2$O (500 mL) with stirring. The solution was cooled to 0-5° C. in an ice bath, and acetyl chloride (83.6 g, 1.07 mol) was added dropwise with the temperature kept below 10° C. during the addition. After the addition was complete, the reaction mixture was stirred for a period of time of about 1.5 hours under ice bath cooling conditions. The ice bath was then removed, and the reaction was stirred for a period of time of about five hours at room temperature. The crude product precipitated from the reaction mixture.

The reaction mixture was added to 500 mL portions of $H_2O$ and $CH_2Cl_2$ in a 2000 mL separatory funnel. The aqueous layer was separated, and the organic layer was washed twice with 500 mL each of $H_2O$. The organic layer was separated, dried over anhydrous $MgSO_4$, and filtered through a column of acidic alumina to remove excess pyridine. Solvent was removed under reduced pressure, to provide a crystalline solid. Yield=112.7 g (83%); M.P.=104° C. (Lit.=102-104° C.). $^1$H NMR (CDCl$_3$) δ 8.2 (m, 2, Ar—H), 7.2 (d, 1, Ar—H), 7.0 (t, 1, Ar—H), 4.0 (t, 2, N—CH$_2$), 3.2 (t, 2, Ar—CH$_2$), 2.2 (3, s, CH$_3$); $^{13}$C NMR (CDCl$_3$) δ 169, 142, 131, 127, 124, 123, 116, 48, 27, 24; IR (neat) 2959, 1643, 1594, 1481, 1398, 1342, 1262, 1016, 766 cm$^{-1}$.

Preparation of Anaerobic Curable Compositions

The following components listed in the table below were used to make anaerobic curable compositions for evaluation:

| Materials | 1 (phr) | 2 (phr) |
| --- | --- | --- |
| PEGMA | 100 | 52.5 |
| Urethane block copolymer | — | 47.5 |
| Radical inhibitor solution | 0.42 | 0.42 |
| Chelator solution | 2.1 | 2.1 |
| Saccharin | 1.05 | 1.05 |
| Hydroperoxide | 0.9 | 0.9 |
| Aromatic amine or amide | 1-2 | 1-2 |

Two base formulations were thus prepared, one based on polyethylene glycol dimethacrylate ("PEGMA") and the other based on a combination of PEGMA and urethane-acrylate block copolymer. The remaining components make up the anaerobic cure system, with the accelerator varied as to identity as set forth below. The aromatic amine or amide was used in an equimolar amount; that is within the range of 1-2 percent by weight.

Fifteen nut and bolt specimens of steel and stainless steel were assembled for each formulation tested. For the break/prevail adhesion tests, the specimens were maintained at ambient temperature for 15 minutes, 1 hour, and 24 hours after assembly. The break and prevail torque strengths (measured in in.-lbs.) were then recorded after 15 minutes, 1 hour, and 24 hours at room temperature (25° C.) and 45-50% relative humidity, respectively. The break torque strengths (also measured in in.-lbs.) were then recorded after 15 minutes, 1 hour, and 24 hours at room temperature (25° C.) and 45-50% relative humidity, respectively.

Each of these formulations was also applied to fifteen replicates of steel pins and collars (having been degreased), and maintained at ambient temperature for 15 minutes, 1 hour, and 24 hours at room temperature (25° C.) and 45-50% relative humidity, respectively.

Break torque is the initial torque required to decrease or eliminate the axial load in a seated assembly. Prevail torque, after initial breakage of the bond, is measured at any point during 360° rotation of the nut. Prevail torque is normally determined at 180° rotation of the nut. Steel and stainless steel ⅜×16 nuts and bolts were degreased with 1,1,1-trichloroethylene, adhesive was applied to the bolt, and the nut was screwed onto the bolt.

The torque strengths were measured using a calibrated automatic torque analyzer. The data for the evaluations is set forth below in the tables and in the Figures.

Figure 1:
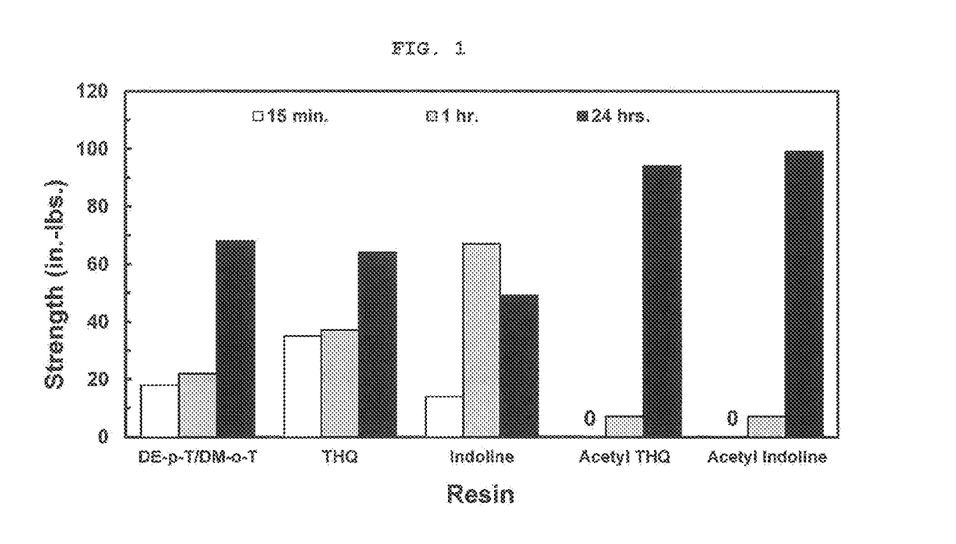
FIG. 1 depicts a plot of break strength vs. time of anaerobic adhesive compositions, some of which using the inventive cure accelerators, on steel nuts and bolts.

In Table 1 below, the breakaway strength (measured in in.-lbs. after the noted time interval) on steel nut and bolt assemblies for Formulation 1 with the various accelerators is shown.

TABLE 1

|  | 15 min. (in. lbs.) | 1 hr. (in. lbs.) | 24 hrs. (in. lbs.) |
| --- | --- | --- | --- |
| DE-p-T/DM-o-T | 18 | 22 | 68 |
| THQ | 35 | 37 | 64 |
| Indoline | 14 | 67 | 49 |
| Acetyl THQ | 0 | 7 | 94 |
| Acetyl Indoline | 0 | 7 | 99 |

These data are shown graphically with reference to FIG. 1.

Figure 2:
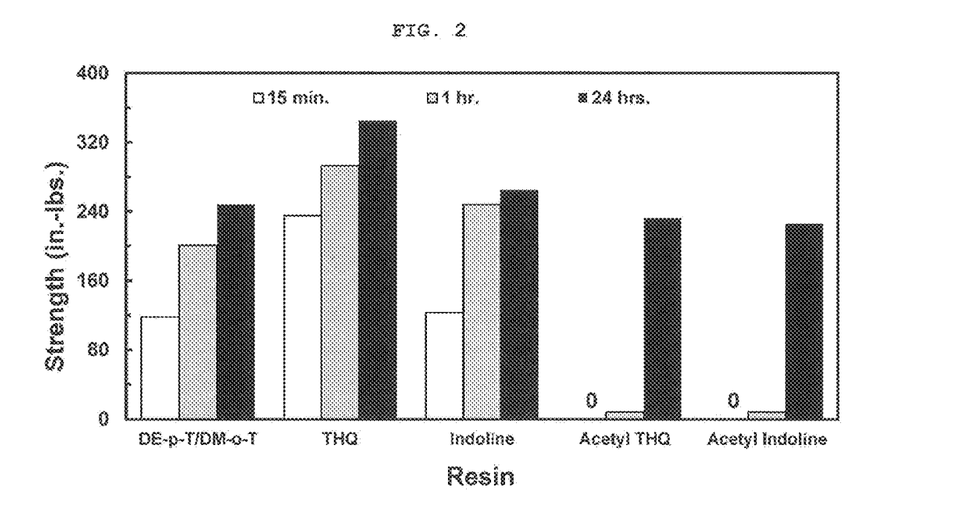
FIG. 2 depicts a plot of prevail strength vs. time of anaerobic adhesive compositions, some of which using the inventive cure accelerators, on steel nuts and bolts.

In Table 2 below, the prevail strength (measured in in.-lbs. after the noted time interval) on steel nut and bolt assemblies for Formulation 1 with the various accelerators is shown.

TABLE 2

|  | 15 min. (in. lbs.) | 1 hr. (in. lbs.) | 24 hrs. (in. lbs.) |
| --- | --- | --- | --- |
| DE-p-T/DM-o-T | 118 | 201 | 248 |
| THQ | 235 | 293 | 345 |
| Indoline | 123 | 248 | 265 |
| Acetyl THQ | 0 | 8 | 232 |
| Acetyl Indoline | 0 | 8 | 226 |

These data are shown graphically with reference to FIG. 2.

Figure 3:
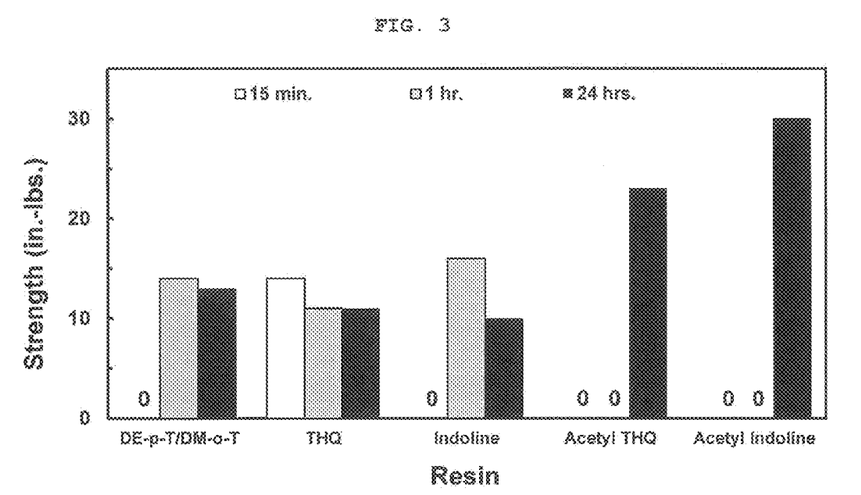
FIG. 3 depicts a plot of break strength vs. time of anaerobic adhesive compositions, some of which using the inventive cure accelerators, on stainless steel nuts and bolts.

In Table 3 below, the breakaway strength (measured in in.-lbs. after the noted time interval) on stainless steel nut and bolt assemblies for Formulation 1 with the various accelerators is shown.

TABLE 3

|  | 15 min. (in. lbs.) | 1 hr. (in. lbs.) | 24 hrs. (in. lbs.) |
| --- | --- | --- | --- |
| DE-p-T/DM-o-T | 0 | 14 | 13 |
| THQ | 14 | 11 | 11 |
| Indoline | 0 | 16 | 10 |
| Acetyl THQ | 0 | 0 | 23 |
| Acetyl Indoline | 0 | 0 | 30 |

These data are shown graphically with reference to FIG. 3.

Figure 4:
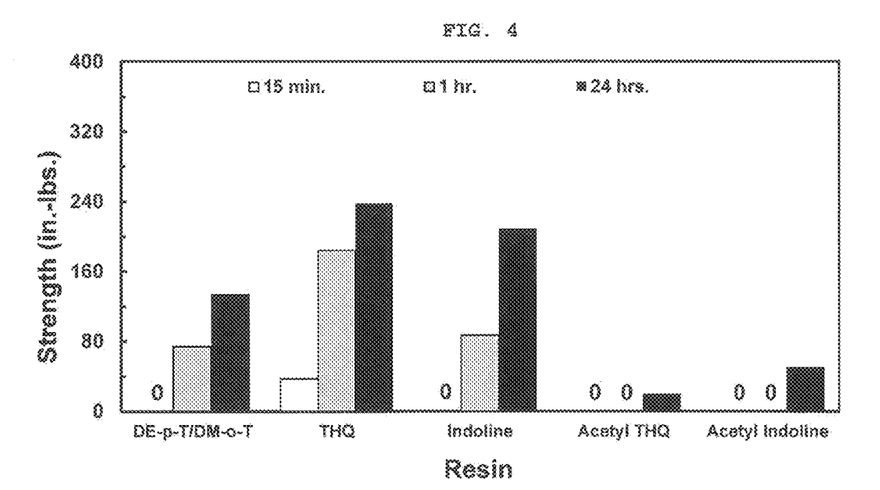
FIG. 4 depicts a plot of prevail strength vs. time of anaerobic adhesive compositions, some of which using the inventive cure accelerators, on stainless steel nuts and bolts.

In Table 4 below, the prevail strength (measured in in.-lbs. after the noted time interval) on stainless steel nut and bolt assemblies for Formulation 1 with the various accelerators is shown.

TABLE 4

|  | 15 min. (in. lbs.) | 1 hr. (in. lbs.) | 24 hrs. (in. lbs.) |
| --- | --- | --- | --- |
| DE-p-T/DM-o-T | 0 | 74 | 134 |
| THQ | 37 | 184 | 238 |
| Indoline | 0 | 87 | 209 |

TABLE 4-continued

|  | 15 min. (in. lbs.) | 1 hr. (in. lbs.) | 24 hrs. (in. lbs.) |
| --- | --- | --- | --- |
| Acetyl THQ | 0 | 0 | 20 |
| Acetyl Indoline | 0 | 0 | 51 |

These data are shown graphically with reference to FIG. 4.

Figure 5:
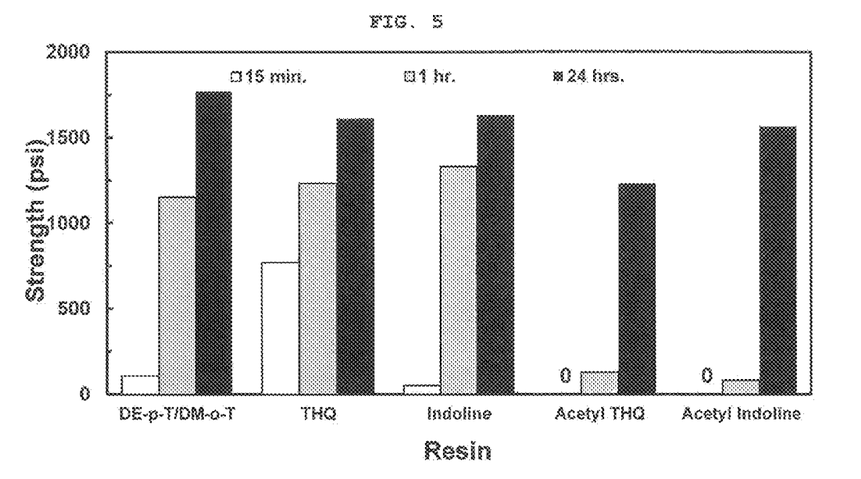
FIG. 5 depicts a plot of tensile strength vs. time of anaerobic adhesive compositions, some of which using the inventive cure accelerators, on steel pins and collars.

In Table 5 below, the tensile strength (measured in in.-lbs. after the noted time interval) on steel pin and collar assemblies for Formulation 1 with the various accelerators is shown.

TABLE 5

|  | 15 min. (psi) | 1 hr. (psi) | 24 hrs. (psi) |
| --- | --- | --- | --- |
| DE-p-T/DM-o-T | 106 | 1152 | 1843 |
| THQ | 770 | 1232 | 1611 |
| Indoline | 49 | 1330 | 1629 |
| Acetyl THQ | 0 | 127 | 1229 |
| Acetyl Indoline | 0 | 81 | 1564 |

These data are shown graphically with reference to FIG. 5.

Figure 6:
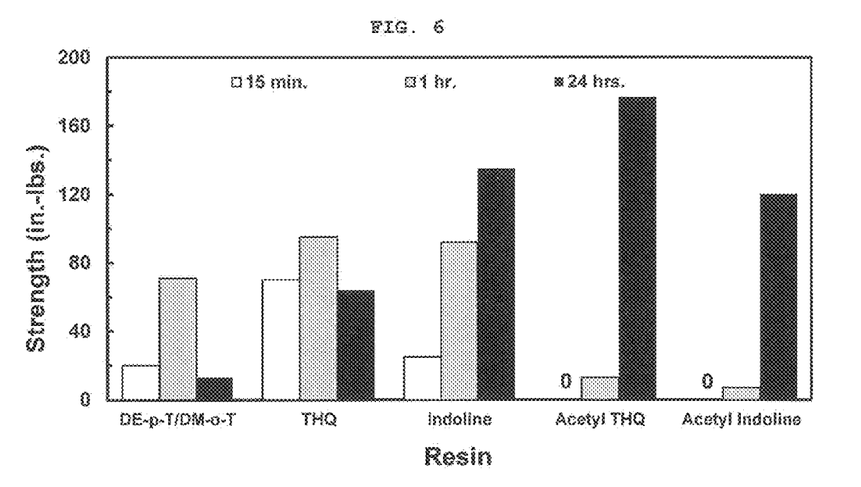
FIG. 6 depicts a plot of break strength vs. time of anaerobic adhesive compositions, some of which using the inventive cure accelerators, on steel nuts and bolts.

In Table 6 below, the breakaway strength (measured in in.-lbs. after the noted time interval) on steel nut and bolt assemblies for Formulation 2 with the various accelerators is shown.

TABLE 6

|  | 15 min. (in. lbs.) | 1 hr. (in. lbs.) | 24 hrs. (in. lbs.) |
| --- | --- | --- | --- |
| DE-p-T/DM-o-T | 20 | 71 | 13 |
| THQ | 70 | 95 | 64 |
| Indoline | 25 | 92 | 135 |
| Acetyl THQ | 0 | 13 | 180 |
| Acetyl Indoline | 0 | 7 | 120 |

These data are shown graphically with reference to FIG. 6.

Figure 7:
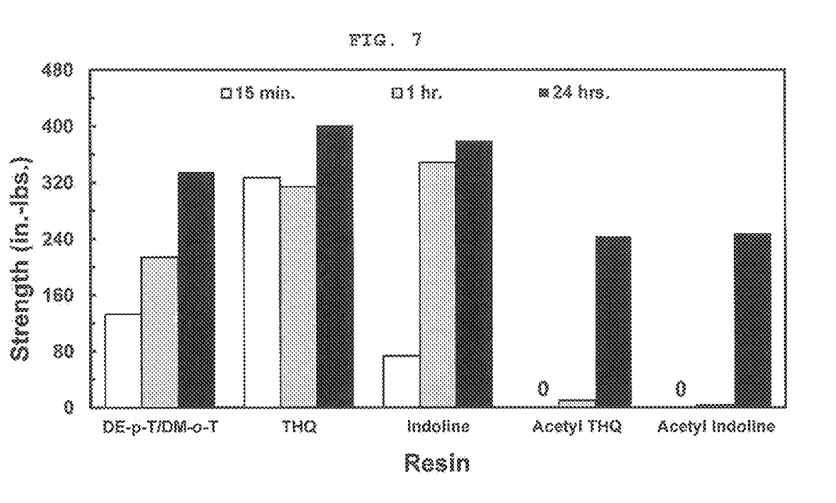
FIG. 7 depicts a plot of prevail strength vs. time of anaerobic adhesive compositions, some of which using the inventive cure accelerators, on steel nuts and bolts.

In Table 7 below, the prevail strength (measured in in.-lbs. after the noted time interval) on steel nut and bolt assemblies for Formulation 2 with the various accelerators is shown.

TABLE 7

|  | 15 min. (in. lbs.) | 1 hr. (in. lbs.) | 24 hrs. (in. lbs.) |
| --- | --- | --- | --- |
| DE-p-T/DM-o-T | 133 | 214 | 335 |
| THQ | 327 | 314 | 401 |
| Indoline | 73 | 348 | 379 |
| Acetyl THQ | 0 | 9 | 243 |
| Acetyl Indoline | 0 | 3 | 247 |

These data are shown graphically with reference to FIG. 7.

Figure 8:
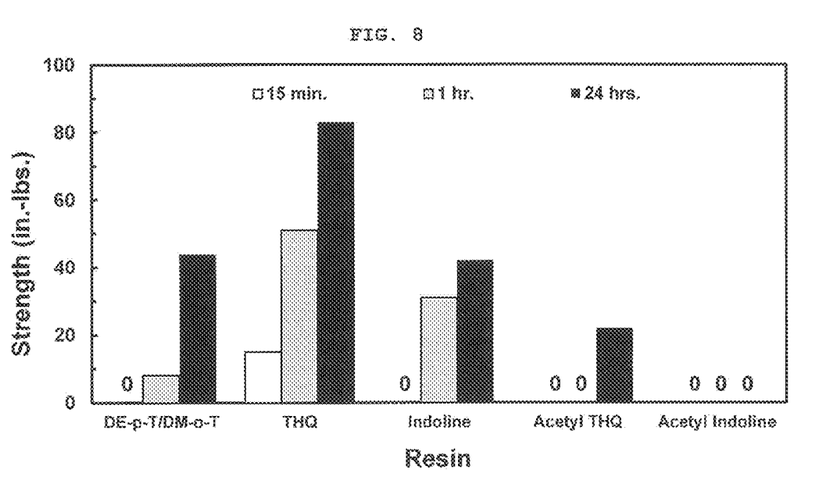
FIG. 8 depicts a plot of break strength vs. time of anaerobic adhesive compositions, some of which using the inventive cure accelerators, on stainless steel nuts and bolts.

In Table 8 below, the breakaway strength (measured in in.-lbs. after the noted time interval) on stainless steel nut and bolt assemblies for Formulation 2 with the various accelerators is shown.

TABLE 8

|  | 15 min. (in. lbs.) | 1 hr. (in. lbs.) | 24 hrs. (in. lbs.) |
| --- | --- | --- | --- |
| DE-p-T/DM-o-T | 0 | 8 | 44 |
| THQ | 15 | 51 | 83 |
| Indoline | 0 | 31 | 42 |
| Acetyl THQ | 0 | 0 | 22 |
| Acetyl Indoline | 0 | 0 | 0 |

These data are shown graphically with reference to FIG. 8.

Figure 9:
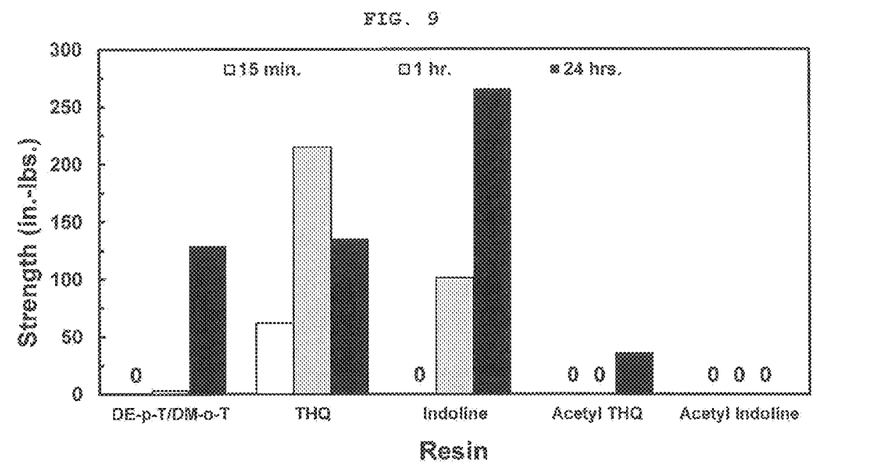
FIG. 9 depicts a plot of prevail strength vs. time of anaerobic adhesive compositions, some of which using the inventive cure accelerators, on stainless steel nuts and bolts.

In Table 9 below, the prevail strength (measured in in.-lbs. after the noted time interval) on stainless steel nut and bolt assemblies for Formulation 2 with the various accelerators is shown.

TABLE 9

|  | 15 min. (in. lbs.) | 1 hr. (in. lbs.) | 24 hrs. (in. lbs.) |
| --- | --- | --- | --- |
| DE-p-T/DM-o-T | 0 | 3 | 129 |
| THQ | 62 | 215 | 135 |
| Indoline | 0 | 101 | 266 |
| Acetyl THQ | 0 | 0 | 36 |
| Acetyl Indoline | 0 | 0 | 0 |

These data are shown graphically with reference to FIG. 9.

Figure 10:
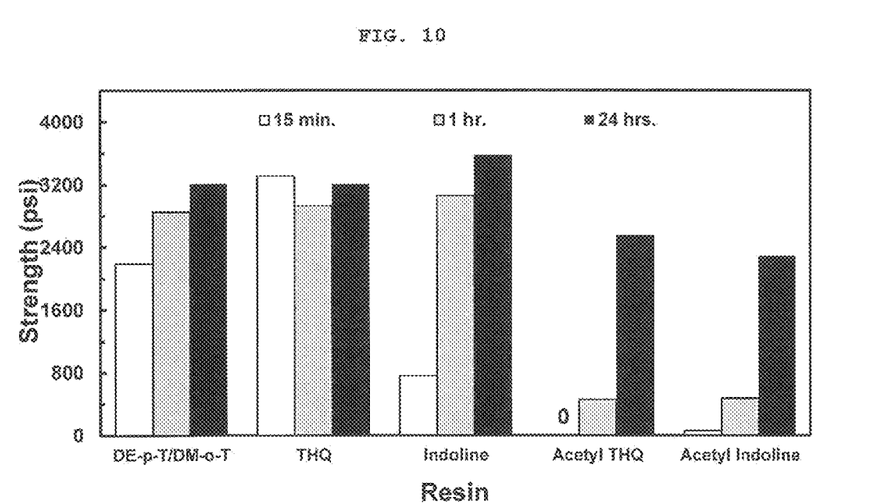
FIG. 10 depicts a plot of tensile strength vs. time of anaerobic adhesive compositions, some of which using the inventive cure accelerators, on steel pins and collars.

In Table 10 below, the tensile strength (measured in in.lbs. after the noted time interval) on steel nut and bolt assemblies for Formulation 2 with the various accelerators is shown.

TABLE 10

|  | 15 min. (psi) | 1 hr. (psi) | 24 hrs. (psi) |
| --- | --- | --- | --- |
| DE-p-T/DM-o-T | 2189 | 2853 | 3212 |
| THQ | 3310 | 2930 | 3205 |
| Indoline | 760 | 3056 | 3580 |
| Acetyl THQ | 0 | 453 | 2555 |
| Acetyl Indoline | 59 | 471 | 2289 |

These data are shown graphically with reference to FIG. 10.

This data indicates that formulations in accordance with this invention exhibited acceptable break and prevail properties at room temperature, but are in some instances somewhat less active when compared to traditional anaerobic adhesives having been applied and cured on the steel or stainless steel substrates. However, the lower odor exhibited by the inventive formulations coupled with expected reduced toxicity of the constituents may lead to less rigorous regulatory requirements and as a result may prove useful in some commercial applications and environments.

Shelf Life Stability

The 82° C. stability of the formulations was determined according to an evaluation in which the formulation is judged to have acceptable shelf stability if the adhesive formulation remains liquid for 3 hours or longer at 82° C. The formulations containing either N-acetyl THQ or N-acetyl indoline were evaluated at 82° C., as were formulations containing the toluidine package and THQ and indoline themselves. Each formulation remained liquid for greater than 24 hours at this temperature.

What is claimed is:

1. An anaerobic curable composition comprising
(a) a (meth) acrylate component;
(b) an anaerobic cure-inducing composition; and
(c) an aromatic amide shown in structure I wherein R and R" are each independently $C_{1-10}$ alkyl, and R' is H or $C_{1-10}$ alkyl, or R and R' together form a four to seven membered ring fused to the benzene ring, and wherein R''' is optional, but when R''' is present, R''' is halogen, alkyl, alkenyl, cycloalkyl, hydroxyalkyl, hydroxyalkenyl, alkoxy, amino, alkylene- or alkenylene-ether, alkylene (meth) acrylate, carbonyl, carboxyl, nitroso, sulfonate, hydroxyl or haloalkyl.

2. The composition according to claim 1, wherein the anaerobic cure-inducing composition comprises a hydroperoxide selected from the group consisting of cumene hydroperoxide, para-menthane hydroperoxide, t-butyl hydroperoxide, t-butyl perbenzoate, benzoyl peroxide, dibenzoyl peroxide, 1,3-bis(t-butylperoxyisopropyl)benzene, diacetyl peroxide, butyl 4,4-bis(t-butylperoxy)valerate, p-chlorobenzoyl peroxide, t-butyl cumyl peroxide, t-butyl perbenzoate, di-t-butyl peroxide, dicumyl peroxide, 2,5-dimethyl-2,5-di-t-butylperoxyhexane, 2,5-dimethyl-2,5-di-t-butyl-peroxyhex-3-yne, 4-methyl-2,2-di-t-butylperoxypentane, t-amyl hydroperoxide, 1,2,3,4-tertramethylbutyl hydroperoxide and combinations thereof.

3. The composition according to claim 1, further comprising at least one accelerator.

4. The composition according to claim 3, wherein the accelerator is selected from the group consisting of amines, amine oxides, sulfimides, metals and sources thereof, acids, and mixtures thereof.

5. The composition according to claim 3, wherein the accelerator is selected from the group consisting of triazines, ethanolamine, diethanolamine, triethanolamine, N,N-dimethyl aniline, benzene sulphonimide, cyclohexyl amine, triethyl amine, butyl amine, saccharin, N,N-diethyl-p-toluidine, N,N-dimethyl-o-toluidine, and acetyl phenylhydrazine with maleic acid, and mixtures thereof.

6. The composition according to claim 1, further comprising at least one stabilizer.

7. The composition according to claim 6, wherein the stabilizer is selected from the group consisting of benzoquinone, naphthoquinone, anthraquinone, hydroquinone, methoxyhydroquinone, butylated hydroxy toluene, ethylene diamine tetraacetic acid or a salt thereof, and mixtures thereof.

8. A method of using as a cure accelerator for anaerobic curable compositions an aromatic amide shown in structure I:

wherein R and R" are each independently $C_{1-10}$ alkyl, and R' is H or $C_{1-10}$ alkyl or R and R' together may form a four to seven membered ring fused to the benzene ring, and wherein R''' is optional, but when R''' is present, R''' is halogen, alkyl, alkenyl, cycloalkyl, hydroxyalkyl, hydroxyalkenyl, alkoxy, amino, alkylene- or alkenylene-ether, alkylene (meth)acrylate, carbonyl, carboxyl, nitroso, sulfonate, hydroxyl or haloalkyl, comprising the steps of:

(a) providing an anaerobic curable composition comprising a (meth)acrylate component and an anaerobic cure-inducing composition;

(b) providing as a cure accelerator for the anaerobic curable composition an aromatic amide shown in structure I:

wherein R and R" are each independently $C_{1-10}$ alkyl, and R' is H or $C_{1-10}$ alkyl or R and R' together may form a four to seven membered ring fused to the benzene ring, and wherein R''' is optional, but when R''' is present, R''' is halogen, alkyl, alkenyl, cycloalkyl, hydroxyalkyl, hydroxyalkenyl, alkoxy, amino, alkylene- or alkenylene-ether, alkylene (meth)acrylate, carbonyl, carboxyl, nitroso, sulfonate, hydroxyl or haloalkyl; and (c) exposing the anaerobic curable composition and the cure accelerator to conditions favorable to cure the composition.

9. The composition of claim 1, wherein the aromatic amide shown in structure I is elected from N-acetyl tetrahydroquinoline, N-acetyl indoline or N-acetyl, N-methyl aniline.

* * * * *